United States Patent
Salo et al.

(10) Patent No.: US 7,194,307 B2
(45) Date of Patent: Mar. 20, 2007

(54) PACING METHOD AND DEVICE FOR PRESERVING NATIVE CONDUCTION SYSTEM

(75) Inventors: Rodney W. Salo, Fridley, MN (US); Bruce H. KenKnight, Maple Grove, MN (US); Joseph M. Pastore, Oakdale, MN (US); Steven D. Girouard, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 19 days.

(21) Appl. No.: 10/744,952

(22) Filed: Dec. 22, 2003

(65) Prior Publication Data

US 2005/0137633 A1 Jun. 23, 2005

(51) Int. Cl.
*A61N 1/368* (2006.01)
(52) U.S. Cl. ............................................. 607/27; 607/9
(58) Field of Classification Search ................. 607/9, 607/24, 27, 28, 15
See application file for complete search history.

(56) References Cited

U.S. PATENT DOCUMENTS

| | | | |
|---|---|---|---|
| 5,016,630 A | 5/1991 | Moberg | |
| 5,190,035 A | 3/1993 | Salo et al. | |
| 5,237,992 A | 8/1993 | Poore | |
| 5,282,838 A * | 2/1994 | Hauser et al. | 607/9 |
| 5,284,491 A | 2/1994 | Sutton et al. | |
| 5,374,281 A | 12/1994 | Kristall et al. | |
| 5,690,689 A * | 11/1997 | Sholder | 607/24 |
| 5,702,424 A * | 12/1997 | Legay et al. | 607/9 |
| 5,782,886 A | 7/1998 | Kuiper et al. | |
| 5,861,011 A | 1/1999 | Stoop | |
| 5,891,175 A | 4/1999 | Walmsley et al. | |
| 5,968,081 A * | 10/1999 | Levine | 607/9 |
| 5,991,659 A | 11/1999 | de Vries et al. | |
| 6,070,101 A * | 5/2000 | Struble et al. | 607/9 |
| 6,141,586 A * | 10/2000 | Mower | 607/9 |
| 6,161,042 A | 12/2000 | Hartley et al. | |
| 6,240,313 B1 * | 5/2001 | Esler | 600/516 |
| 6,246,909 B1 | 6/2001 | Ekwall | |
| 6,459,928 B2 * | 10/2002 | Mika et al. | 600/510 |
| 6,708,061 B2 * | 3/2004 | Salo et al. | 607/9 |
| 6,748,261 B1 * | 6/2004 | Kroll et al. | 600/510 |
| 6,904,317 B2 * | 6/2005 | Florio et al. | 607/9 |
| 2002/0082663 A1 * | 6/2002 | Stahmann et al. | 607/27 |
| 2004/0082973 A1 * | 4/2004 | Kim et al. | 607/9 |

* cited by examiner

*Primary Examiner*—George R. Evanisko
*Assistant Examiner*—Michael Kahelin
(74) *Attorney, Agent, or Firm*—Schwegman, Lundberg, Woessner & Kluth, P.A.

(57) ABSTRACT

An implantable device for delivering cardiac pacing therapy in order to improve cardiac function is programmed to allow some amount of intrinsic activity to occur without otherwise the disturbing the pacing algorithm used to deliver therapy. Intrinsic cardiac cycles utilize the heart's native conduction system and thus serve to prevent the atrophy which may otherwise result from continuous pacing.

18 Claims, 2 Drawing Sheets

PACING METHOD AND DEVICE FOR PRESERVING NATIVE CONDUCTION SYSTEM

FIELD OF THE INVENTION

This patent application pertains to methods and apparatus for the treatment of cardiac disease. In particular, it relates to methods and apparatus for improving cardiac function with electro-stimulatory therapy.

BACKGROUND

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac, a type of therapy referred to herein as cardiac function therapy (CFT). The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence via the His-Purkinje network to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection an intrinsic atrial contraction.

SUMMARY OF THE INVENTION

The specialized His-Purkinje conduction network of the normal heart rapidly conducts excitatory impulses from the atrio-ventricular node to the ventricular myocardium to result in a coordinated contraction of both ventricles. Artificial pacing with an electrode fixed into an area of the myocardium does not take advantage of the heart's native conduction system for conducting excitation throughout the ventricles, however, because the His-Purkinje network can only be entered by impulses emanating from the atrio-ventricular node. Atrophy of the His-Purkinje system may result from a prolonged period of disuse where there is a lack of electrical impulses propagating through the system. It has been shown that some patients with chronic bradycardia who have been treated with continuous pacing therapy no longer have functional His-Purkinje conductive tissue distal to the site at which paces are delivered. In some cases, the cells of the system are replaced by fibrous tissue (i.e. fibrosis), and is therefore incapable of propagating electrical impulses.

As noted above, cardiac function therapy may involve pacing the heart for purposes other than to enforce a particular rhythm. Such patients may, for example, be chronotropically competent and have an intact AV conduction pathway. In patients for whom such therapy is not intended be permanent and who have intact AV conduction pathways, degeneration of those pathways is an unfortunate side-effect. The present invention is directed toward a solution of this problem by providing a device for delivering pacing therapy in order to improve cardiac function which is programmed to allow some amount of intrinsic activity to occur without otherwise the disturbing the pacing algorithm used to deliver therapy. Intrinsic cardiac cycles utilize the heart's native conduction system and thus serve to prevent the atrophy which may otherwise result from continuous pacing. In one embodiment, the device is programmed to maintain a specified ratio of paced to intrinsic cycles by temporarily discontinuing pacing for specified or variable time intervals.

DETAILED DESCRIPTION

Figure 1:
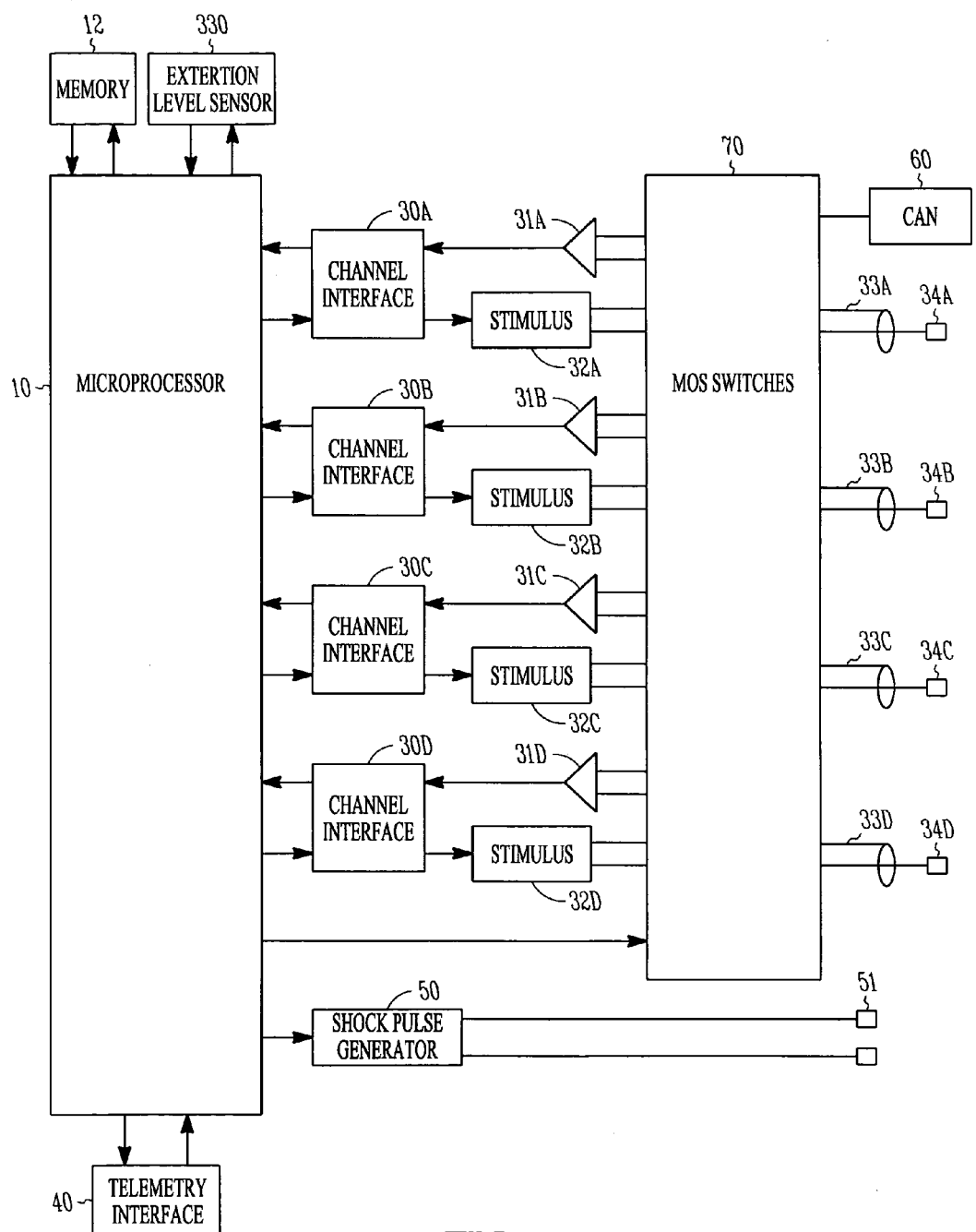
FIG. 1 is a system diagram of a cardiac device configured for multi-site stimulation and sensing.

As noted above, many patients now receive pacemakers for non-traditional indications (e.g., cardiac resynchronization therapy) where ventricular pacing is applied while all or part of the patient's native conduction system is intact. In these patients, one would like to pace the ventricle by a method that preserves the native conduction (His-Purkinje) system. What follows are descriptions of cardiac function therapy and an exemplary implantable device for delivering such therapy. Exemplary algorithms for promoting native conduction during the delivery of cardiac function therapy are then presented.

1. Cardiac Function Therapy

One example of electro-stimulatory therapy for the purpose of improving cardiac function is CRT. In ventricular resynchronization therapy, the ventricles are paced at more than one site in order to effect a spread of excitation that results in a more coordinated contraction and thereby overcome interventricular or intraventricular conduction defects. Biventricular pacing is one example of resynchronization therapy in which both ventricles are paced in order to synchronize their respective contractions. Resynchronization therapy may also involve multi-site pacing applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist.

Another type of cardiac function therapy is stress reduction pacing which involves altering the coordination of ventricular contractions with multi-site pacing in order to change the distribution of wall stress experienced by the ventricle during the cardiac pumping cycle. The degree to which a heart muscle fiber is stretched before it contracts is termed the preload. The maximum tension and velocity of shortening of a muscle fiber increases with increasing preload. The increase in contractile response of the heart with increasing preload is known as the Frank-Starling principle. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region that contracts later than other regions is subjected to both an increased preload and afterload. This situation is created frequently by the ventricular conduction delays associated with heart failure and ventricular dysfunction. The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress. The parts of the myocardium that contract earlier in the cycle, on the other hand, are subjected to less stress and are less likely to undergo hypertrophic remodeling.

The degree of wall stress experienced by a myocardial site during systole is thus dependent upon the time at which that site contracts relative to other myocardial sites. Reversal of remodeling may be effected by pacing one or more sites in a ventricle (or an atrium) with one or more excitatory stimulation pulses during a cardiac cycle with a specified pulse output sequence. The spread of excitation from a ventricular pacing site is not conducted by the His-Purkinje system but must proceed only via the much slower conducting ventricular muscle fibers, resulting in the part of the ventricular myocardium stimulated by the pacing electrode contracting well before parts of the ventricle located more distally to the electrode. Pacing therapy can therefore be delivered in a manner that excites one or more previously stressed and remodeled regions of the myocardium earlier during systole so that they experience less afterload and preload. Pre-excitation of a remodeled region relative to other regions unloads the region from mechanical stress and allows reversal of remodeling to occur.

2. Exemplary Implantable Device

An implantable cardiac device is typically placed subcutaneously or submuscularly in a patient's chest with leads threaded intravenously into the heart to connect the device to electrodes used for sensing and stimulation. Leads may also be positioned on the epicardium by various means. A programmable electronic controller causes the stimulus pulses to be output in response to lapsed time intervals and sensed electrical activity (i.e., intrinsic heart beats not as a result of a stimulus pulse). The device senses intrinsic cardiac electrical activity by means of internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a stimulus pulse (a.k.a. a pace or pacing pulse when delivered in order to enforce a certain rhythm) with energy above a certain threshold is delivered to the chamber.

FIG. 1 shows a system diagram of a microprocessor-based cardiac device suitable for practicing the present invention. The device is equipped with multiple sensing and pacing channels which may be physically configured to sense and/or pace multiple sites in the atria or the ventricles. The device shown in FIG. 1 can be configured for cardiac resynchronization pacing of the atria or ventricles and/or for myocardial stress reduction pacing such that one or more cardiac sites are sensed and/or paced in a manner that pre-excites at least one region of the myocardium. The multiple sensing/stimulation channels may be configured, for example, with one atrial and two ventricular sensing/stimulation channels for delivering biventricular resynchronization therapy, with the atrial sensing/stimulation channel used to deliver biventricular resynchronization therapy in an atrial tracking mode as well as to pace the atria if required. The controller 10 of the pacemaker is a microprocessor which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in the figure are four exemplary sensing and pacing channels designated "a" through "d" comprising bipolar leads with ring electrodes 34*a*–*d* and tip electrodes 33*a*–*d*, sensing amplifiers 31*a*–*d*, pulse generators 32*a*–*d*, and channel interfaces 30*a*–*d*. Each channel thus includes a pacing channel made up of the pulse generator connected to the electrode and a sensing channel made up of the sense amplifier connected to the electrode. The channel interfaces 30*a*–*d* communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The electrodes of each bipolar lead are connected via conductors within the lead to a MOS switching network 70 controlled by the microprocessor. The switching network is used to configure a sensing channel by switching electrodes to the input of a sense amplifier in order to detect intrinsic cardiac activity and configure a pacing channel by switching electrodes to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 60 serving as a ground electrode. As explained below, one way in which the device may alter the spatial distribution of pacing is to switch from unipolar to bipolar pacing (or vice-versa) or to interchange which electrodes of a bipolar lead are the cathode and anode during bipolar pacing. A shock pulse generator 50 is also interfaced to the controller for delivering a defibrillation shock via a pair of shock electrodes 51 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. A sensing channel may also be configured to record an electrogram for morphology analysis, where the electrogram may be an intracardiac electrogram generated by a sensing/pacing electrode within the heart or a so-called subcutaneous ECG generated by a subcutaneously disposed electrode. A telemetry interface 40 is also provided which enables the controller to communicate with an external programmer.

An exertion level sensor 330 (e.g., an accelerometer, a minute ventilation sensor, or other sensor that measures a parameter related to metabolic demand) enables the controller to adapt the pacing rate in accordance with changes in the patient's physical activity. In one embodiment, the exertion level sensor is a minute ventilation sensor which includes an exciter and an impedance measuring circuit. The exciter supplies excitation current of a specified amplitude (e.g., as a pulse waveform with constant amplitude) to excitation electrodes that are disposed in the thorax. Voltage sense electrodes are disposed in a selected region of the thorax so that the potential difference between the electrodes while excitation current is supplied is representative of the transthoracic impedance between the voltage sense electrodes. The conductive housing or can may be used as one of the voltage sense electrodes. The impedance measuring circuitry processes the voltage sense signal from the voltage sense electrodes to derive the impedance signal. Further processing of the impedance signal allows the derivation of signal representing respiratory activity and/or cardiac blood volume, depending upon the location the voltage sense electrodes in the thorax. (See, e.g., U.S. Pat. Nos. 5,190,035 and 6,161,042, assigned to the assignee of the present invention and hereby incorporated by reference.) If the impedance signal is filtered to remove the respiratory component, the result is a signal that is representative of blood volume in the heart at any point in time, thus allowing the computation of stroke volume and, when combined with heart rate, computation of cardiac output.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. An AV delay interval, for example, is a ventricular escape interval started by an atrial sense in an atrial tracking mode and started by an atrial pace in an AV sequential pacing mode Cardiac function therapy, whether for the purpose of cardiac resynchronization or for reversal of remodeling, is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites.

A particular pacing mode for delivering cardiac function therapy, whether for stress reduction or resynchronization, includes a defined pulse output configuration and pulse output sequence, where the pulse output configuration specifies a specific subset of the available electrodes to be used for delivering pacing pulses and the pulse output sequence specifies the timing relations between the pulses. The pulse output configuration is defined by the controller selecting particular pacing channels for use in outputting pacing pulses and by selecting particular electrodes for use by the channel with switch matrix 70. The pulse output configuration and sequence which optimally effects reverse remodeling by selectively reducing myocardial wall stress may or may not be the optimum pulse output configuration and sequence for maximizing hemodynamic performance by resynchronizing ventricular contractions. For example, a more hemodynamically effective contraction may be obtained by exciting all areas of the myocardium simultaneously, which may not effectively promote reversal of the hypertrophy or remodeling.

3. Pacing Algorithms for Preserving Native Conduction System

The present invention involves the promotion of impulses from the native His-Purkinje system in a pacemaker patient by programming an implantable device to reduce the extent of ventricular pacing at fixed or variable intervals so that His-Purkinje cells continue to be stimulated and do not undergo atrophy or fibrosis. Reduction of the extent of ventricular pacing may involve the temporary complete withdrawal of pacing therapy or, in the case of a chronotropically incompetent patient, temporary reversion to an atrial-only pacing mode. In another variation, reduction of the extent of pacing may be effected by the device prolonging the paced AV interval in an atrial tracking or AV sequential pacing mode or other ventricular escape interval so that more intrinsic ventricular beats occur after atrial events or so that more partially intrinsic or fusion beats (i.e., beats made up of both intrinsic and paced excitation) occur which partially activate the native His-Purkinje system.

These different means for reducing the extent of pacing may be implemented in different ways as in the embodiments described below.

Figure 2:
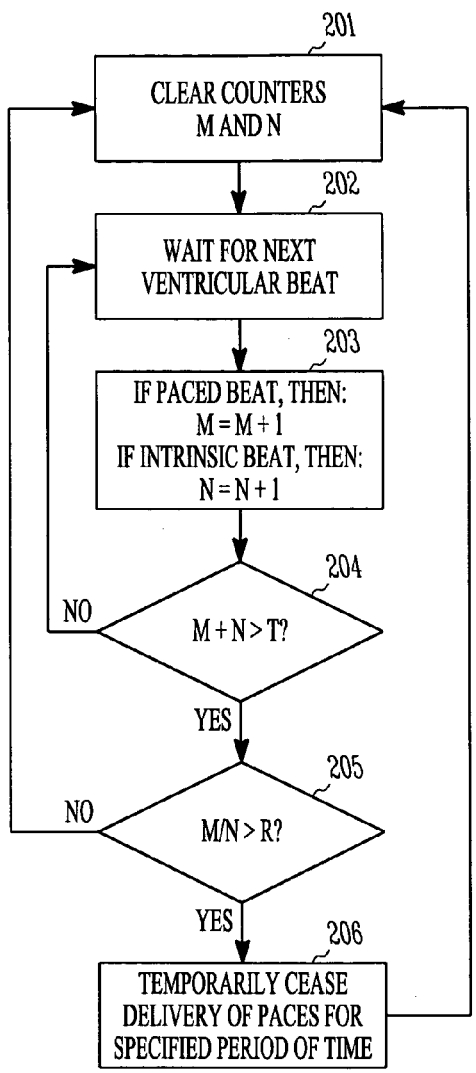
FIG. 2 illustrates an exemplary algorithm for implementing the invention.

In a one embodiment, a cardiac function device is programmed to allow a certain maximum ratio of paced beats to intrinsic conducted beats. The ratio may also be programmably specified by a clinician. FIG. 2 illustrates an exemplary algorithm for maintaining a specified maximum ratio R of paced to intrinsic beats. At step 201, the device clears counters M and N which are used to maintain counts of paced and intrinsic beats, respectively. At step 202, the device waits for the next beat to occur. At step 203, either M or N is incremented depending on whether the beat is paced or intrinsic, respectively. At step 204, the total number of counted beats is compared with a specified number T which represents how many beats must be counted before the ratio is computed and compared with R. In an alternate embodiment, beats may be counted for a specified period of time before the ratio is computed and tested. At step 205, the ratio M/N of paced to intrinsic beats over the previous total T beats (or, alternatively, over a specified time period) is computed and compared with the desired ratio R. If the computed M/N ratio is less than or equal to R, the device returns to step 201. If the computed ratio is greater than the desired maximum value R, the extent of pacing is reduced at step 206. After the period during which the extent of pacing is reduced ends, the device returns to step 201.

In another embodiment, the device is programmed to enable intrinsic beats by reducing the extent of pacing for a certain amount of time per day (e.g. 1 hour per day) or other time period. (e.g., 12 hours per week). The amount of time for which the extent of pacing is reduced may be made to increase if the computed M/N ratio is greater than R. The times when the extent of pacing is reduced may be selected to coincide with the times at which specific events such as sleep or exercise are expected to occur. Alternatively, the device may use an exertion level sensor to detect periods of activity or non-activity and then reduce the extent of pacing accordingly. Whether it is desirable to reduce the extent of pacing as part of cardiac function therapy while the patient is active or while the patient is at rest will largely depend on the purpose of the cardiac function therapy. In cases where the cardiac function therapy is intended to increase cardiac output (i.e., CRT), it may be desirable to reduce the extent of therapy only when the patient is non-active. If the therapy is intended to redistribute wall stress for reversal of cardiac remodeling, on the other hand, such therapy may not be hemodynamically enhancing so that reduction of the extent of such therapy may most advantageously take place when the patient is active. The device may also have the capability of measuring cardiac output so that temporary reductions in the extent of pacing may take place as determined by the level of cardiac output rather than activity level.

In another embodiment, the state of the patient's conduction system is assessed by determining the patient's interventricular conduction delay. An increased interventricular conduction delay indicates a worsening of the patient's conduction system. An implantable device may determine the interventricular conduction delay by measuring the interval between right and left ventricular senses during a cardiac cycle or by measuring the width of a ventricular depolarization waveform (i.e., an R wave or QRS wave) in an electrogram. If the patient's conduction system is found to be worsening, the extent of reduction in pacing can be increased and vice-versa. For example, the maximum ratio R paced to intrinsic beats may be dynamically determined by the implantable device assessing the conduction velocity during one or more intrinsic beats from a recorded intracardiac or subcutaneous electrogram or by measuring the time interval between senses of differently placed ventricular sensing electrodes. If the conduction velocity shows progressive slowing, it may be assumed that deterioration of the native conduction system is occurring. The device may then increase the proportion of intrinsic beats to counteract this process. For example, the device may be programmed to record an electrogram during an intrinsic beat and dynamically adjust the desired maximum ratio of paced to intrinsic beats in accordance with a measured width of a depolarization wave in the electrogram such that the desired maximum ratio is decreased if the measured width increases.

In another embodiment, rather than temporarily reducing the extent of pacing, the device may be configured to deliver pacing therapy in a manner which promotes intrinsic activity. For example, in the case where the patient has an implanted device configured for biventricular pacing, the device may be programmed to periodically switch between right ventricular pacing and left ventricular pacing with a long enough AV delay to guarantee intrinsic activation of the non-paced ventricle. This would be done often enough to guarantee that both conduction systems (right and left side) remain healthy.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable cardiac device, comprising:
   one or more sensing channels for sensing cardiac electrical activity at one or more myocardial sites;
   one or more pacing channels for delivering pacing pulses to one or more myocardial sites;
   a controller for controlling the delivery of pacing pulses in accordance with a demand pacing mode; and,
   wherein the controller is programmed to count the number of paced and intrinsic beats over a defined time interval and to intermittently reduce the extent of pacing in order to maintain a desired maximum ratio of paced to intrinsic beats and to dynamically adjust the desired maximum ratio of paced to intrinsic beats in accordance with a determination of an amount of interventricular conduction delay such that the desired maximum ratio is decreased if the amount of interventricular conduction delay increases.

2. The device of claim 1 wherein the controller is programmed to intermittently reduce the extent of pacing by discontinuing pacing for a specified period of time.

3. The device of claim 1 wherein the controller is programmed to intermittently reduce the extent of pacing by lengthening an escape interval.

4. The device of claim 3 wherein the escape interval is an AV delay interval.

5. The device of claim 1 wherein the controller is programmed to record an electrogram during an intrinsic beat and dynamically adjust the desired maximum ratio of paced to intrinsic beats in accordance with a measured width of a depolarization wave in the electrogram such that the desired maximum ratio is decreased if the measured width increases.

6. The device of claim 1 wherein the controller is programmed to reduce the extent of pacing for a certain amount of time per specified time period, where the amount of time for which the extent of pacing is reduced varies with how the count of intrinsic and paced beats compares with the desired maximum ratio.

7. The device of claim 6 wherein the times when the extent of pacing is reduced coincide with times at which sleep is expected to occur.

8. The device of claim 1 further comprising an exertion level sensor and wherein the extent of pacing is reduced in accordance with a measured exertion level.

9. The device of claim 1 further comprising:
sensing and pacing channels for the right and left ventricles; and
wherein the controller is programmed to measure the time interval between right and left ventricular senses during a cardiac cycle and adjust the desired maximum ratio of paced to intrinsic beats in accordance therewith.

10. A method for operating an implantable cardiac device, comprising:
sensing cardiac electrical activity at one or more myocardial sites;
delivering pacing pulses in accordance with a demand pacing mode;
counting the number of paced and intrinsic beats over a defined time interval;
intermittently reducing the extent of pacing in order to maintain a desired maximum ratio of paced to intrinsic beats; and,
dynamically adjusting the desired maximum ratio of paced to intrinsic beats in accordance with a determination of an amount of interventricular conduction delay such that the desired maximum ratio is decreased if the amount of interventricular conduction delay increases.

11. The method of claim 10 further comprising intermittently reducing the extent of pacing by discontinuing pacing for a specified period of time.

12. The method of claim 10 further comprising intermittently reducing the extent of pacing by lengthening an escape interval.

13. The method of claim 12 wherein the escape interval is an AV delay interval.

14. The method of claim 10 further comprising recording an electrogram during an intrinsic beat and dynamically adjusting the desired maximum ratio of paced to intrinsic beats in accordance with a measured width of a depolarization wave in the electrogram such that the desired maximum ratio is decreased if the measured width increases.

15. The method of claim 10 further comprising reducing the extent of pacing for a certain amount of time per specified time period, where the amount of time for which the extent of pacing is reduced varies with how the count of intrinsic and paced beats compares with the desired maximum ratio.

16. The method of claim 15 wherein the times when the extent of pacing is reduced coincide with times at which sleep is expected to occur.

17. The method of claim 10 further comprising reducing the extent of pacing in accordance with a measured exertion level.

18. The method of claim 10 further comprising:
sensing the right and left ventricles; and
measuring the time interval between right and left ventricular senses during a cardiac cycle and adjust the desired maximum ratio of paced to intrinsic beats in accordance therewith.

* * * * *